(12) United States Patent
Rittenhouse-Olson

(10) Patent No.: US 7,374,755 B2
(45) Date of Patent: May 20, 2008

(54) THERAPEUTIC USE OF ANTI-TF-ANTIGEN ANTIBODY

(75) Inventor: Kate Rittenhouse-Olson, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/190,165

(22) Filed: Jul. 26, 2005

(65) Prior Publication Data

US 2006/0018913 A1    Jan. 26, 2006

Related U.S. Application Data

(60) Provisional application No. 60/591,011, filed on Jul. 26, 2004.

(51) Int. Cl.
*A61K 39/395* (2006.01)

(52) U.S. Cl. ................... 424/130.1; 424/138.1

(58) Field of Classification Search ..................... None
See application file for complete search history.

(56) References Cited

OTHER PUBLICATIONS

Gura (1997, Science 278:1041-1042).*
Freshney (Culture of Animal Cells, A Manual of Basic Technique, Alan R. Liss, Inc., 1983, New York, p. 4).*
(Roitt et al., Immunology, Third Edition (Mosby, London England) p. 1.7).*
Canevari et al. (1994, Annals of Oncology, 1994, 5:698-701).*
Harris et al (1993, TIBTECH 11:42-44).*
White et al. (2001, Ann. Rev. Med. 52:125-145).*
Dermer et al. (Bio/Technology, 1994, 12:320).*
Osband et al. (Immunol. Today, 11:193-195, 1990).*
Tockman et al (Cancer Res., 1998, (Suppl), 52:2711s-2718).*
Busken, C et al, (Digestive Disease Week Abstracts and Itinerary Planner, 2003, abstract No. 850).*

Glinsky, et al., The Role of Thomsen-Friedenreich Antigen in Adhesion of Human Breast and Prostate Cancer Cells to the Endothelium, Cancer Research 61, Jun. 15, 2001, pp. 4851-4857.
Springer, et al., Proposed Molecular Basis of Murine Tumor Cell-Hepatocyte Interaction, The Journal of Biological Chemistry, vol. 258, No. 9, Issue of May 10, 1983, pp. 5702-5706.
Khaldoyanidi, et al., MDA-MB-435 Human Breast Carcinoma Cell Homo- and Heterotypic Adhesion under Flow Conditions Is Mediated in Part by Thomsen-Friedenreich Antigen-Galectin-3 Interactions, The Journal of Biological Chemistry, vol. 278, No. 6, Issue of Feb. 7, 2003, pp. 4127-4134.
Landon, et al., Combinatorial Evolution of High-Affinity Peptides that Bind to the Thomsen-Friedenriech Carcinoma Antigen, Journal of Protein Chemistry, vol. 22, No. 2, Feb. 2003, pp. 193-204.
Rittenhouse-Diakun, et al.; Development and Characterization of Monoclonal Antibody to T-Antigen: (Galbetal-3GalNac-alpha-O); Hybridome, vol. 17, No. 2, 1998; pp. 165-173.
Shigeoka, et al.; Inhibition of liver mestastases from neuraminidase-treated colon 26 cells by an anti-Thomsen-Friedenreich-specific monoclonal antibody; Tumour Biol. 1999, vol. 20, No. 3; 1 page (abstract).
Springer; Immunoreactive T and Tn epitopes in cancer diagnosis, prognosis, and immunotherapy; J. Mol. Med. 1997, vol. 75; pp. 594-602.

* cited by examiner

*Primary Examiner*—Misook Yu
*Assistant Examiner*—Mark Halvorson
(74) *Attorney, Agent, or Firm*—Hodgson Russ LLP

(57) ABSTRACT

The invention is related to administration of monoclonal antibody JAA-F11 to an individual for inhibition of metastasis and/or inhibition of growth of cells which express TF-Ag, or for detection of tumors or metastatic foci which express TF-Ag. For inhibition of metastasis or inhibition of growth of cells expressing TF-Ag, the method comprises administering to the individual a therapeutic amount of mAb JAA-F11, wherein the JAA-F11 mAb inhibits the metastasis and/or growth of the TF-Ag expressing cancer cells. For detection of tumors or metastatic foci, mAb JAA-F11 is conjugated to a detectable label and administered to the individual. Detection of the label identifies metatstatic foci or tumors which comprise cancer cells expressing TF-Ag.

10 Claims, 7 Drawing Sheets

THERAPEUTIC USE OF ANTI-TF-ANTIGEN ANTIBODY

This application claims priority to U.S. provisional application No. 60/591,011, filed on Jul. 26, 2004, the disclosure of which is incorporated herein by reference.

This invention was supported by grant number R15AI49210-01 from the National Institutes of Health. The Government has certain rights in the invention.

FIELD OF THE INVENTION

The present invention relates generally to the inhibition of cancer cell growth and metastasis. More particularly, the invention relates to the use of a monoclonal antibody to inhibit metastasis of cancer cells in an individual.

BACKGROUND OF THE INVENTION

During carcinogenesis, alterations occur in the biosynthesis of carbohydrate structures on the cell surface, and several different carbohydrates linked either to proteins or to lipids have been recognized to be tumor-associated antigens. TF-Antigen (TF-Ag) is a tumor-associated antigen of several carcinomas, including breast, lung, bladder, prostate and pancreas (1-4). TF-Ag has been proposed to be involved in the metastatic process (5-10).

TF-Ag is Galactose$\beta$1-3 N-Acetyl Galactosamine, a disaccharide attached to a protein by an alpha O-serine or O-threonine linkage. TF-Ag was discovered by Thomsen, Friedenreich and Hueber in the late 1920's (2). TF-Ag is hidden on various normal cell membranes because it is linked to other carbohydrates, either by tertiary structures or by highly negative-charged sialic acid (3,7). The densities of TF-Ag predict the histologic grade of carcinomas (9,11), the invasive potential, and the probability of early recurrence in breast (2,12-13), urinary bladder, and prostatic carcinoma (14).

TF-Ag is more than an immunopathologic marker; it is postulated to have a role in adhesion and metastasis (2). Reversible or irreversible adhesion is a primary step of invasion (15) and may occur when the TF-Ag adhesion molecules recognize ligands such as galectins or other lectins (4,16). There is an increased expression of TF-Ag in metastatic tumors, and lectins that bind TF-Ag are in common sites of metastatic tumor growth (17). Ligands for TF-Ag adhesion have been found in the vascular endothelium, the liver, the bone marrow and the lymph nodes (18-19) and this may explain how TF-Ag levels are related to carcinoma aggressiveness (20).

There have been reports concerning the immunotherapeutic value of an induced immune response to carbohydrate tumor associated antigens (8,26-29). For example, O'Boyle et al show development of very low level IgG and IgM responses to two antigens which are related to TF-Ag, Tn (GalNAc) and sialylated Tn (NANA$\alpha$2-6GalNAc) in colon cancer patients (26-27). Longenecker's studies in breast cancer patients used a keyhole limpet hemocyanin (KLH) conjugate of sialyl Tn and obtained higher responses and observed some clinical response in these patients (29-30). Springer and Desai used vaccination with a T/Tn vaccine composed of types O and MN red blood cell derived glycoproteins which resulted in improved breast cancer patient survival although only small amounts of IgM were made (15). Immunization of breast cancer patients with Globo H (a hexasaccharide which contains TF-Ag), conjugated to KLH injected with the adjuvant QS21 to improve immunogenicity resulted in most patients forming only an IgM response (31). However, IgM is generally of lower affinity and specificity than IgG, and represents a less mature immune response, and many previous studies relating to antibodies to TF-Ag involve IgM antibodies. Further, some anti-TF-Ag antibodies are not clinically useful because they cause undesirable proliferation of tumor cells (45). Moreover, while peptides which can bind to TF-Ag and inhibit cell adhesion in vitro have been described (5), it has also been found that some peptides which can bind to the TF-Ag on human carcinoma cell lines and interfere with cell aggregation exhibit a low monomeric affinity for the TF-Ag, and therefore cannot be dissolved at high concentration in aqueous buffers, which significantly limit their potential use (Landon et al., Journal of Protein Chemistry, (2003) Vol. 22: pp 193-204).

One study purported to investigate the effect of a monoclonal antibody to TF-Ag on cancer cells in a mouse model (Shigeoka, et al. Tumor Biology (1999) 20: 138-146). However, that study attempted to simulate metastasis by direct injection into the liver of cancer cells that were pre-incubated with the monoclonal antibody before being injected. Nodule formation in the livers of mice injected with the cells pre-incubated with the monoclonal antibody were compared to mice receiving injections with cancer cells that were not pre-incubated with the monoclonal antibody. While there were fewer nodules in mice receiving the pre-incubated cells, this study did not provide a relevant model of antibody-mediated inhibition of metastasis because, due to the pre-incubation of the cancer cells with the monoclonal antibody, there was no requirement for the antibody to travel through the body to locate and bind to cells expressing the TF-Ag. Further, there was no assessment as to whether the nodule formation was the result of cancer cells traveling through the endothelium in a manner similar to the natural metastatic process or whether the nodules were simply the result of lodging and proliferation of the injected cells.

Finally, while the production and characterization of another anti TF-Ag monoclonal antibody has been described (21), none of the aforementioned studies demonstrate that the use of a monoclonal antibody to TF-Ag would inhibit either metastasis or growth of cancer cells in an individual.

SUMMARY OF THE INVENTION

In the present invention is provided a method for inhibiting metastasis of cancer cells in an individual, a method for inhibiting the growth of cancer cells in an individual and a method for detecting metastatic foci or tumors in an individual. The methods are related in that they entail the use of a monoclonal antibody (mAb) JAA-F11 to target cancer cells in vivo, which cancer cells express TF-Ag molecules.

In this regard, the method of inhibiting metastasis comprises administering to the individual a therapeutic amount of mAb JAA-F11, wherein the JAA-F11 mAbs inhibit the metastasis of TF-Ag expressing cancer cells. JAA-F11 mAbs may be administered alone, in combination with chemotherapeutic agents to which the mAbs are not conjugated, or conjugated to a chemotherapeutic agent. For example, JAA-F11 mAbs may be conjugated to any of a variety of enzymatically active toxins and fragments thereof, or to cytotoxic radioisotopes.

The method for inhibiting the growth of cancer cells in an individual comprises administration of a therapeutic amount of mAb JAA-F11 to the individual, wherein the JAA-F11 mAbs inhibit the growth of cancer cells which express TF-Ag. As in the method for inhibiting metastasis, when JAA-F11 mAbs are administered to inhibit the growth of cancer cells which express TF-Ag, the JAA-F11 mAbs may be administered alone, in combination with chemotherapeutic agents to which the mAbs are not conjugated, or conjugated to chemotherapeutic agents.

In another embodiment is provided a method for identifying in an individual metastatic foci, tumors, or combinations thereof. The method comprises the steps of administering to the individual JAA-F11 mAbs, wherein the mAbs have been conjugated to a detectable label, and detecting the detectable label to identify the metatstatic foci or tumors. For example, the mAbs may be conjugated to a spin label for use in magnetic resonance imaging (MRI).

DESCRIPTION OF THE FIGURES

In FIGS. 2A and 2B, the inhibition of the adhesion to HUVEC monolayer (FIG. 2A) and human bone marrow endothelial cells HBMEC-60 (FIG. 2B) in static adhesion experiments is shown. In FIG. 2C, the effect of JAA-F11 on MDA-MB-435 rolling in well-differentiated microvessels of perfused porcine dura mater ex vivo is shown. In the graphs, * designates P<0.05 and ** P<0.01 respectively.

FIG. 6A shows lungs from mice in the PBS control group.

DESCRIPTION OF THE INVENTION

Figure 1:
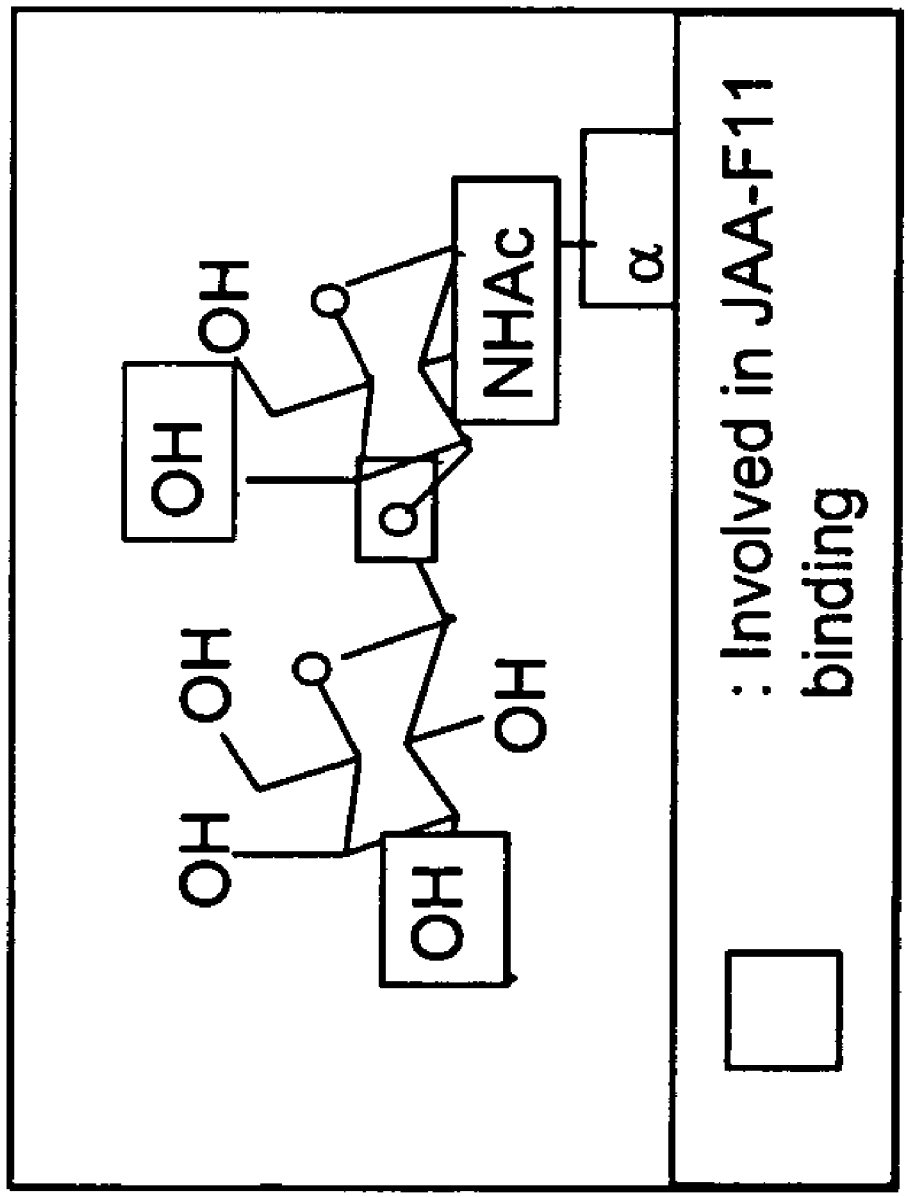
FIG. 1 is a schematic representation of the regions of TF-Ag determined to be important for binding to JAA-F11.

In the present invention is provided a method of inhibiting metastasis of cancer cells in an individual, which cancer cells express TF-Ag molecules. The method comprises administering to the individual a therapeutic amount of JAA-F11 mAbs wherein administration of the JAA-F11 mAbs inhibits the metastasis of the TF-Ag expressing cancer cells The hybridmoma that produces JAA-F11 mAb was deposited pursuant to the Budapest Treaty requirements with the American Type Culture Collection (ATCC), 10801 University Boulevard, Manassas, Va., 20110, on Sep. 25, 2007, and has been assigned Patent Deposit Designation PTA-8652.

In another embodiment, a method is provided for inhibiting in an individual the growth of cancer cells which express TF-Ag. The method comprises administering to the individual an amount of JAA-F11 mAbs effective to inhibit the growth of cancer cells expressing TF-Ag.

In another embodiment is provided a method for identifying in an individual metastatic foci, tumors, or combinations thereof, wherein the metastatic foci or tumors comprise cells expressing TF-Ag. The method comprises the steps of administering to the individual JAA-F11 mAbs, wherein the JAA-F11 mAbs have been conjugated to a detectable label, and detecting the detectable label to identify metatstatic foci, tumors, or combinations thereof.

We have determined that mAb JAA-F11 does not bind to GM1, a glycolipid expressed on the surface of many cell types, including the central nervous system. This is in contrast to a previously described mAb to TF-Ag, termed "170H82," which binds to TF-Ag and GM1 (22). Therefore, this broader reactivity of the 170H82 mAb would result in reaction with normal tissues that contain GM1, whereas mAb JAA-F11 does not. Thus, mAb JAA-F11 is more specific for cancer cells than other TF-Ag mAbs. Further, we have also determined that JAA-F11 does not cause proliferation of cells, unlike other anti-TF-Ag antibodies that have been reported (45).

In one embodiment, the present invention contemplates making a "humanized" mAb JAA-F11 for use in the method of inhibiting metastasis of cells which express TF-Ag or in the method of inhibiting the growth of cells which express TF-Ag. "Humanized" forms of non-human (e.g., mice) antibodies are chimeric antibodies that contain minimal sequence derived from the non-human antibody. Humanized antibodies are essentially human immunoglobulins (also called the "recipient" antibody) in which residues from a hypervariable region of the recipient are replaced by residues from a hypervariable region of a non-human species (also called a "donor" antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also can comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Methods for humanizing non-human antibodies are well known in the art. Humanization of mAb JAA-F11 can be essentially performed following the method of Winter and co-workers by substituting mouse CDR sequences for the corresponding sequences of a human antibody (Jones et al., Nature, 321:522-525 (1986); Riechmann et al., Nature, 332:323-327 (1988); Verhoeyen et al., Science, 239:1534-1536 (1988)).

In another embodiment, an antigen-binding or variable region fragment of mAb JAA-F11 may be used in the method of the invention. Examples of suitable antibody fragments include mAb JAA-F11 Fab, Fab', F(ab')$_2$, and Fv fragments. Various techniques have been developed for the production of antibody fragments. Traditionally, these fragments were derived via proteolytic digestion of intact antibodies (see, e.g., Morimoto et al, Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries. Alternatively, Fab'-SH fragments can be directly recovered from *E. coli* and chemically coupled to form F(ab')2 fragments (Carter et al., Bio/Technology 10: 163-167 (1992)). According to another approach, F(ab')2 fragments can be isolated directly from recombinant host cell culture. Other techniques for the production of mAb JAA-F11 fragments will be apparent to the skilled practitioner.

In another embodiment, JAA-F11 mAbs may be conjugated to a chemotherapeutic agent to enable localization of the chemotherapeutic agent to cancer cells via-binding of the conjugated JAA-F11 mAbs to cells expressing TF-Ag. Chemotherapeutic agents useful in the generation of such antibody conjugates include enzymatically active toxins and fragments thereof. Suitable enzymatically active toxins include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

Conjugates of the JAA-F11 mAbs and chemotherapeutic agents may be made using a variety of bifunctional protein coupling agents such as N-succinimidyl-3-(2-pyriyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared essentially as described in Vitetta et al. Science 238: 1098 (1987).

In another embodiment, the JAA-F11 mAbs may be conjugated to a radioactive agent. A variety of radioactive isotopes are available for conjugating to JAA-F11 mAbs such that cells to which the JAA-F11 mAbs bind may be imaged or selectively destroyed. For selective destruction of cells expressing TF-Ag, the JAA-F11 mAbs may be conjugated to a highly radioactive atom, such as $In^{111}$, $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

When the JAA-F11 mAb conjugates are used for identifying-cells expressing TF-Ag in metastatic foci or in tumors, the JAA-F11 mAbs conjugates may comprise a radioactive atom for scintigraphic studies, for example $Tc^{99m}$ (metastable technetium-99), $I^{123}$, or a spin label for nuclear magnetic resonance (NMR) imaging (also known as magnetic resonance imaging or "MRI"), such as $I^{123}$, $I^{131}$, $I^{124}$, $F^{19}$, $C^{13}$, $N^{15}$, $O^{17}$ or Gadlinium (III) or Manganese (II).

The radio-labels may be incorporated in the JAA-F11 mAbs in known ways. For example, labels such as $tc^{99m}$ or $I^{123}$, $Re^{186}$, $Re^{188}$ and $In^{111}$ can be attached via a cysteine residue in the JAA-F11 mAbs. $Y^{90}$ can be attached via a lysine residue. The Bolton Hunter method can be used to incorporate $I^{123}$. "Monoclonal Antibodies in Immunoscintigraphy" (Chatal, CRC Press: 1989) describes suitable methods in detail.

The use of antibodies for identification of metastatic foci and/or tumors by in vivo imaging is well known in the art. For example, antibody-chelators labeled with $In^{111}$ have been described for use in the radioimmunoscintographic imaging of carcinoembryonic antigen expressing tumors (Sumerdon et al. Nucl. Med. Biol. 1990 17:247-254). In particular, these antibody-chelators have been used in detecting tumors in patients suspected of having recurrent colorectal cancer (Griffin et al. J. Clin. One. 1991 9:631-640). Antibodies with paramagnetic ions as labels for use in MRI have also been described (Lauffer, R. B. Magnetic Resonance in Medicine 1991 22:339-342). Suitably labeled JAA-F11 mAbs can be used in a similar manner.

Labeled JAA-F11 mAbs can be injected into patients diagnosed with or suspected of having a metastatic disease to identify mestatstic foci and/or tumors. Information from such imaging can be used for diagnosing or staging of the disease status of the patient. The label used can be selected in accordance with the imaging system to be used. For example; $Indium^{111}$, $Technetium^{99}$ or $Iodine^{131}$ can be used for planar scans or single photon emission computed tomography (SPECT). Positron emitting labels such as $Fluorine^{19}$ $Iodine^{123}$ and, $Iodine^{124}$ can be used in positron emission tomography. Paramagnetic ions such as Gadlinium (III) or Manganese (II) can used in magnetic resonance imaging (MRI). Localization of the label within a particular tissue of the individual permits localization of metastatic foci or tumors which comprise cells expressing TF-Ag. A concentration of label at a particular location greater than background permits identification of the presence of metastasized cells. In a preferred embodiment, after administration of labeled JAA-F11 mAbs, a suitable period of time is allowed to pass such that unbound JAA-F11 mAbs are cleared from the individual such that background label is greatly reduced.

Therapeutic formulations comprising conjugated or unconjugated JAA-F11 mAbs may be prepared by mixing with pharmaceutically acceptable carriers, excipients or stabilizers (Remington's Pharmaceutical Sciences 16th edition, Osol, A. Ed. (980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The JAA-F11 mAbs may be administered by any suitable means, including parenteral, subcutaneous, intraperitoneal, intrapulmonary, and intranasal. Parenteral infusions include intramuscular, intravenous, intraarterial, intraperitoneal, intralymphatic or subcutaneous administration. In addition, the JAA-F11 mAbs may suitably be administered by pulse infusion, e.g., with declining doses of the antibody. Preferably, the dosing is given by injections, most preferably intravenous or subcutaneous injections, depending in part on whether the administration is brief or chronic. In preferred embodiments, the JAA-F11 mAbs are administered to an individual diagnosed with or suspected of having breast, colon, prostate, ovarian, bladder or other TF Ag+ cancers to inhibit metastasis or to inhibit the growth of the cancer cells.

One may also administer other compounds, such as chemotherapeutic-agents, immunosuppressive agents and/or cytokines with the JAA-F11 mAbs. The combined administration can include co-administration, using separate formulations or a single pharmaceutical formulation, and can also include consecutive administration in either order, wherein preferably there is a time period while both (or all) active agents simultaneously exert their biological activities.

The JAA-F11 mAbs may be administered to a human or other animal in accordance with the aforementioned methods of treatment in an amount sufficient to inhibit metastasis and/or growth of cells expressing TF-Ag. The JAA-F11 mAbs can be administered to such human or other animal in a conventional dosage form prepared by combining the JAA-F11 mAbs with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables, such as the size of the individual and the stage of the disease.

Dosages of radiolabeled JAA-F11 mAbs will also vary depending on the patient, the antibody specificity, half-life, radioisotope stability, etc., and the extent of disease. Such dosages can be determined by one skilled in the art. In one embodiment, a dosage of 4 mg/kg body weight, or a maintenance dose of 2 mg/kg body weight can be used.

The following Examples are meant to illustrate the invention and are not meant to limit the scope of the claims.

EXAMPLE 1

This Example demonstrates the inhibition of cancer cell adhesion to endothelial and bone marrow cells by monoclonal antibody JAA-F11. Human umbilical vein endothelial cells (HUVEC) were purchased from Cascade Biologics (Portland, Oreg.). The basal Medium 200 (Cascade Biologics) supplemented with low serum growth supplement (LSGS) containing FBS (2% v/v final concentration), hydrocortisone, human fibroblast growth factor, heparin, and human epidermal growth factor was used for the HUVEC. The cells at passages 8-12 were used for the adhesion experiments. The human bone marrow endothelial cell line, HBMEC-60, provided by Dr. C. E. van der Schoot (University of Amsterdam, Amsterdam, the Netherlands), was developed by immortalization of HBMEC originally isolated from adult human bone marrow using the amphotrophic helper-free retrovirus pLXSN16 E6/E7 (32). The HBMEC-60 cells were shown to maintain their normal phenotype and adhesive properties, specifically the ability to bind haematopoietic progenitor cells (32). The basal Medium 200 (Cascade Biologics) supplemented with 20% FBS and LSGS containing hydrocortisone, human fibroblast growth factor, heparin, and human epidermal growth factor was used for HBMEC-60. Cells were maintained in monolayer culture in a humidified incubator (5% $CO_2$) at 37° C.

Adhesion experiments using these cells were performed essentially as previously described (4-5). Briefly, a single cell suspension of cancer cells pre-labeled with 3 µg/ml of acridine orange ($5*10^4$ cells per chamber in 2.5 ml of complete media supplemented with the antibody tested) was added to the monolayer of the endothelial cells grown to confluence directly on microscope slides using 4-well chamber slides (NalgeNunc, Naperville, Ill.). The chambers were sealed, and cells were allowed to adhere for 1 h at 37° C., after which the chambers were inverted for 30 min to allow sedimentation of nonadherent cells. Next, the medium was drained, samples were gently rinsed with PBS, fixed for 30 min in 2% formaldehyde solution in PBS, mounted under cover glass, and examined by fluorescent microscopy, Four random fields in each well were photographed at 250× magnification and the total number of adhered cells in every field was counted. The assay was performed in quadruplicate for each condition. The results depicted in FIG. 2A and FIG. 2B demonstrate the inhibition of adhesion to HUVEC monolayer and human bone marrow endotheliali cells HBMEC-60, respectively.

EXAMPLE 2

This Example demonstrates that monoclonal antibody can block a key stage of metastasis and metastatic tumor formation in an ex vivo mode. To perform these experiments, perfused porcine dura mater was used in adhesion experiments as previously described (33-34). Briefly, dura mater corresponding to one hemisphere, collected from mature female Yucatan miniature: swine (Charles River, Me.) within 30 min after animals sacrifice in accordance with the University of Missouri approved animal care protocol, was dissected and flattened onto a Sylgard-coated 100 mm dish. A major branch of the median meningeal artery was cannulated, and dura vasculature was perfused at 15 µl/min first with Krebs physiological salt supplemented with 1.0 mg/ml porcine serum albumin for 20 min, then with vessel-labeling solution (0.3 µg/ml acridine orange in RPMI-1640 supplemented with 10% FBS and 1.0 mg/ml porcine albumin) for an additional 40 min. Prior to injection, cancer cells were pre-labeled for 5 min with 3 µg/ml acridine orange solution in RPMI-1640 medium, rinsed three times, dissociated from plastic, pipetted to produce a single cell suspension, filtered through a 20 µm nylon mesh to remove cell clumps, and adjusted to $5·10^4$ cell/ml. Interactions of cancer cells with dura microvasculature were monitored and video recorded ar 30 frames per second using a fluorescence video microscopy system based on a Laborlux 8 microscope (Leitz Wetzlar, Germany) equipped with 75-watt xenon lamp and a high sensitivity CCD video camera (COHU, San Diego, Calif.). For subsequent frame-by-frame analysis, the recorded analog video images were digitized using a media converter DVMC-DA2 (Sony, Japan) and Adobe Premier 6 software (Adobe Systems, San Jose, Calif.).

Figure 2:
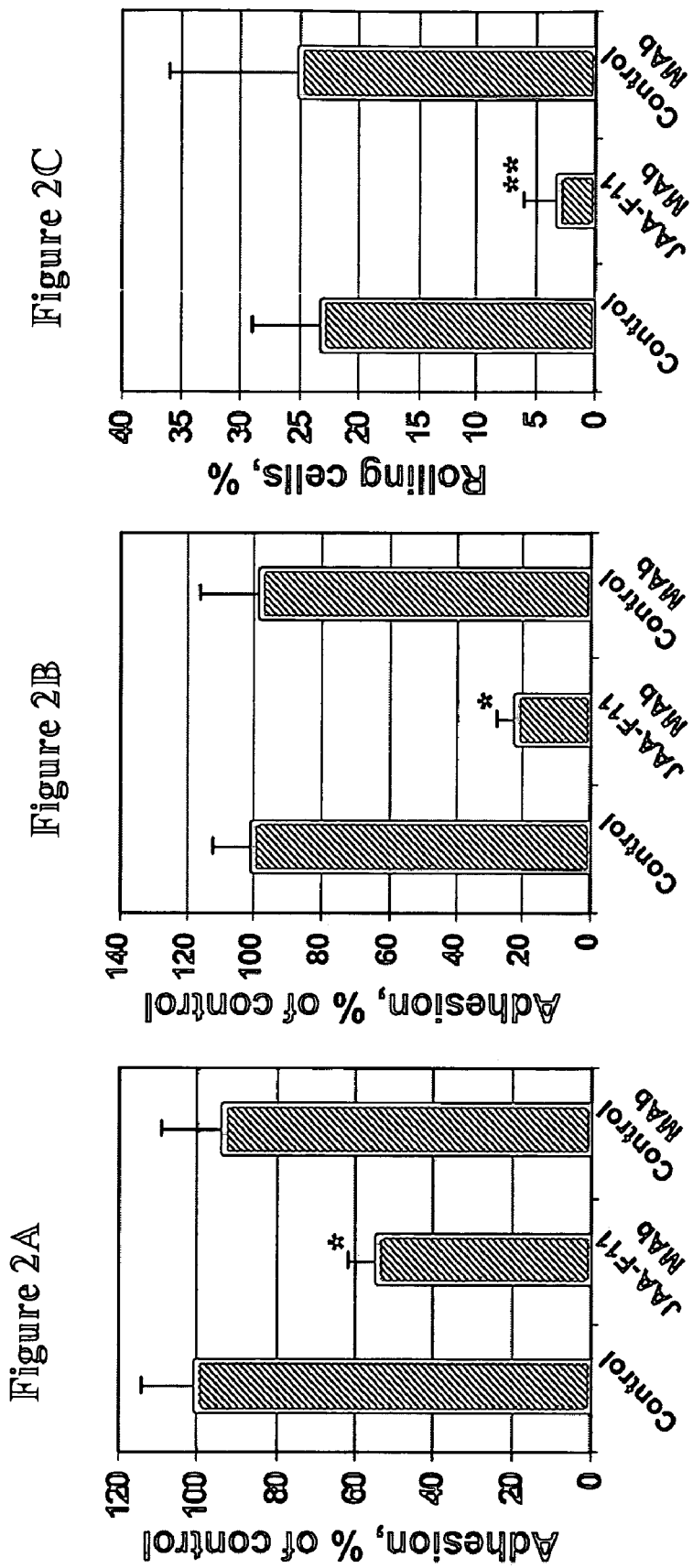
FIG. 2 is a graphical representation of results demonstrating the inhibitory effect of JAA-F11 on breast cancer cell adhesion to endothelium. Experimental results showed the inhibitory effect of JAA-F11 on MIDA-MB-435 metastatic human breast carcinoma cell line adhesion to the endothelium.

The results from these experiments are depicted in FIG. 2C and demonstrate that JAA-F11 blocks human breast tumor cell rolling on porcine dura mater, which is a key stage in the formation of metastatic tumors.

EXAMPLE 3

This Example demonstrates TF-Ag detection on tumor cell lines with JAA-F11 using Indirect Cellular ELISA. To perform these experiments, five mouse cancer cell lines were tested. 4T1 (ATCC Number: CRL-2539) and JC (ATCC Number: CRL-2116) are both from BALB/c strain mammary gland adenocarcinomas. The 4T1 cell line is an animal model for stage IV human breast cancer (35-37). When injected into BALB/c mice, 4T1 spontaneously produces highly metastatic tumors that can metastasize to the lung, liver, lymph nodes and brain while the primary tumor is growing in situ (35-37). JC also are able to produce tumors in BALB/c mice (38). Myeloma (ATCC Number: CRL-1580) is the fusion partner for producing JAA-F11 hybridoma (21), and was used as a TF-Ag-negative control cell line. LL (ATCC Number: CRL-1642) is the Lewis lung carcinoma cell line also from mouse (39-40). The RIF cell line is a radiation-induced fibrosarcoma. Except for the culture medium for LL (Dulbecco's modified Eagle's medium (DMEM) with 4 mM L-glutamine with 1.5 g/L sodium bicarbonate and 4.5 g/L glucose (90%) plus 10% FBS), the other four cell lines were grown in RPMI 1640 medium with 2 mM L-glutamine with 1.5 g/L sodium bicarbonate, 4.5 g/L glucose, 10 mM HEPES and 1.0 mM sodium pyruvate (90%) plus 10% FBS.

To harvest and prepare single-cell suspensions, 4T1, JC, LL and RIF were trypsinized for removal from the flasks. The cell suspensions were placed into 5 ml tubes in triplicate. Four percent formaldehyde was added and incubated for 20 minutes to fix cells. The tubes were centrifuged and the supernatants were decanted. PBS-Tween-1% BSA was added back to each tube to prevent the fixed cells from drying. The tubes with fixed cells were stored at 4° C. overnight or up to two weeks. A peroxidase-linked immunoassay was performed in tubes. Different JAA-F11 antibody-dilutions were added to each tube and incubated for 2 hours at 37° C. After the incubation, the tubes were washed three times with 3 ml wash buffer (PBS-Tween, no azide). Anti-mouse IgG (u-chain specific) peroxidase conjugate at 1:2000 in PBS-Tween-1% BSA was added to each tube, incubated 1 hour at RT, and washed three times. O-phenylenediamine dihydrochloride (Sigma, St. Louis Mo.) was added and after, one hour, 100 μl of the stop solution (1 N $H_2SO_4$) was added to each tube followed by centrifugation for 10 min at 1200 rpm. 200 μl of was transferred into the respective wells in a microtiter plate and the plate was read on a microplate reader at 490 nm, using a well of unreacted substrate as a blank to zero the reader.

Figure 3:
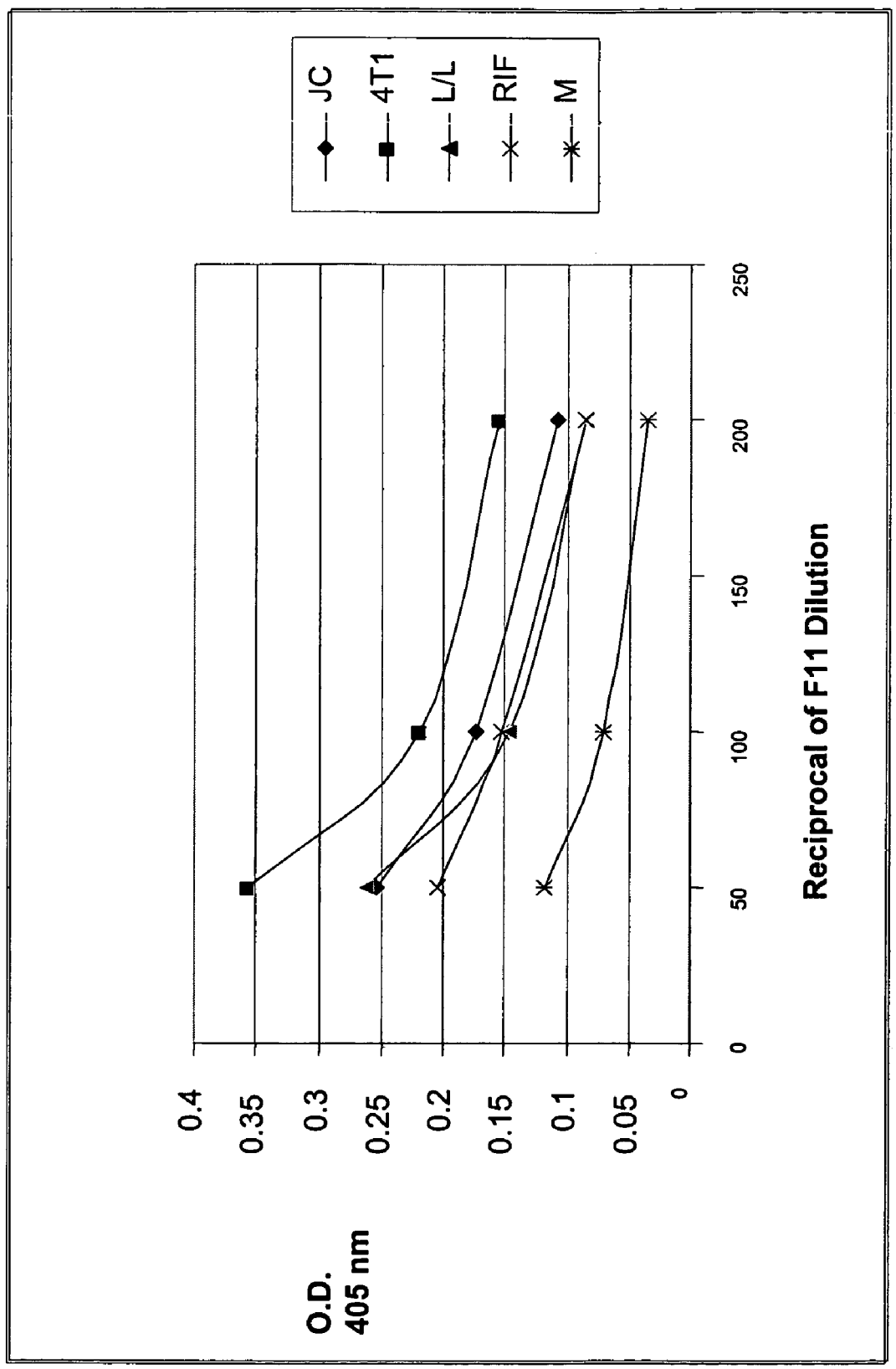
FIG. 3 is a graphical representation of results from a whole cell indirect enzyme immunoassay (EIA) and depicts reactivity of five mouse cancer cells at five different JAA-F11 dilutions. This demonstrates that 4T1 and JC cells are the highest expressors of TF-Ag, followed by LL and RIF, and the myeloma cells are: either negative or very low for TF-Ag expression.

The JC and 4T1 (breast cancer) and LL (lung cancer) cell lines were expected to be positive, and the RIF (fibrosarcoma) cell line and the M (myeloma) cell line were used as negative controls. The binding of various concentrations of JAA-F11 mAb to these cells was measured. The results depicted in FIG. 3 demonstrate reactivity of the five mouse cancer cells at five different JAA-F11 dilutions. The reaction with JAA-F11 was linear. This reaction was also linear with cell number (data not shown). Myeloma cells, as expected, were shown to be negative for TF-Ag expression.

These results demonstrate that mAb JAA-F11 can be used to selectively bind to cancer cells that express TF-Ag, and that breast cancer cells (4T1 and JC) and lung cancer cells (LL) cells are very high expressers of TF-Ag.

EXAMPLE 4

This Example demonstrates the effect of monoclonal antibody JAA-F11 on cell growth. To determine the direct effect of JAA-F11 on tumor cell growth, an in vitro proliferation analysis was performed (41-42). 4T1, Lewis Lung, JC, RIF and Myeloma cells were grown as described in Example 3. The cells were plated at a concentration which was still in the linear portion of the growth curve at 72 hours. Fifty μg/ml of JAA-F11 mAb was added to each of 8 wells of cells for co-culture. Cells in culture medium without Ab and culture medium alone were used as negative controls. After 68 hours of cell growth in 96 well plates at 37° C., 5% $CO_2$, 10 μl of the tetrazolium salt 3-[4,5-Dimethylthiazol-2-yl]-2,5-diphenyl-tetrazolium bromide: thiazoyl blue (MTT) was added to each well of the culture plate and the plates were returned to the incubator for 4 hours, for a total growth time of 72 hours (41-42). At the end of the 72 hr incubation period, the resulting insoluble formazan product in each well was solubilized by adding 120 μl of 5% formic acid in isopropanol with forceful mixing. The absorbance of each well was measured with a microplate reader at 570 nm as an indication of the metabolic activity of the cells.

Figure 4:
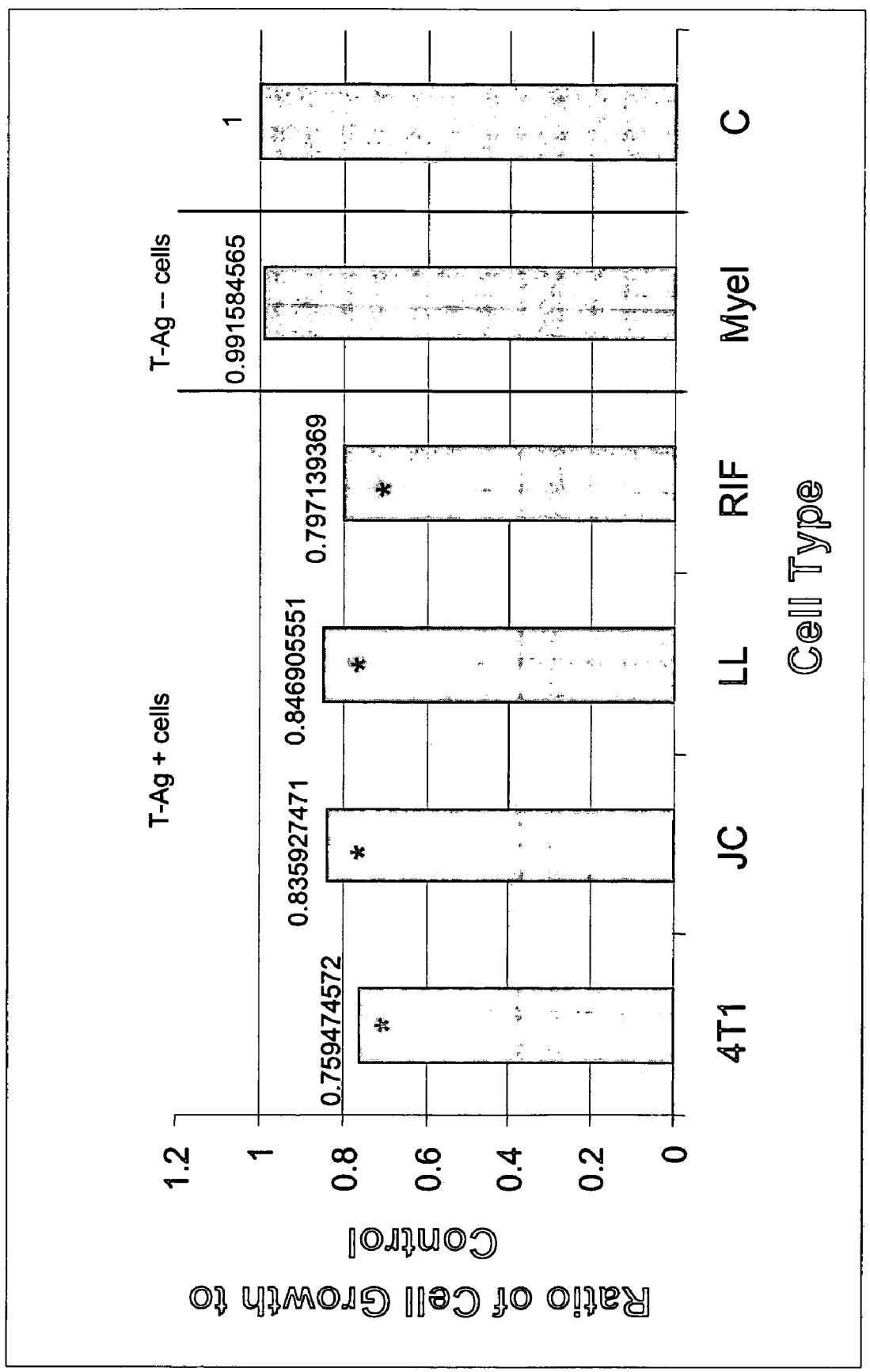
FIG. 4 is a graphical representation of results from cells grown with JAA-F11 antibody relative to cells grown without antibody in an MTT assay (41-42). Cell lines 4T1, JC, Lewis Lung, and RIF (all TF-Ag+), show significant inhibition of growth as indicated by the asterisk while the control cells (Myeloma) do not exhibit growth inhibition.

After performing the assay on three separate days in sets of 8 on each day, an average optical density (O.D.) was obtained. The average of the cells grown with JAA-F11 was statistically compared to cells grown without JAA-F11. A statistically significant decrease in cell growth due to the presence of JAA-F11 was seen in the cell lines found to be TF-Ag positive in Example 3; i.e., 4T1, JC, LL, and RIF ($p<0.05$), but not in the TF-Ag negative myeloma cells. These results are summarized in FIG. 4. The results are expressed as a comparison of the amount of cells growing with JAA-F11 mAb to the same number of cells grown without JAA-F11 mAb.

Thus, this Example demonstrates that JAA-F11 has a statistically significant inhibitory effect (approximately 20%, $p<0.01$, which varied by cell type) on in vitro tumor cell growth; unlike other Abs to TF-Ag, which enhance in vitro tumor growth.

EXAMPLE 5

This Example demonstrates an in vivo anti-metastatic effect of monoclonal antibody JAA-F11. To perform these experiments, the 4T1 mouse breast cancer model was used. The 4T1 tumor line has several characteristics that make it a suitable experimental animal model for human mammary cancer. First, 4T1 tumor cells are TF-Ag positive, easily transplanted into the mammary gland so that the primary tumor can grow in situ, and metastases readily develop. The primary tumor can be surgically removed, so that metastatic disease can be studied in the model, comparable to the clinical situation where the primary breast tumor is surgically removed and metastatic foci may remain intact (35-37).

4T1 tumor cells were cultured with. RPMI 1640 medium containing 2 mM L-glutamine, 1.5 g/L sodium bicarbonate, 4.5 g/L glucose, 10 mM HEPES and 1.0 mM sodium pyruvate (90%) plus 10% FBS in a 37° C., 5% $CO_2$ tissue culture incubator. Cultures were split using standard trypsinization protocols 2 to 3 times per week and were not grown in vitro longer than one month before implantation. According to previous studies, $1 \times 10^4$ viable tumor cells per mouse was selected to ensure the tumor incidence will be 100% but the tumor load will be not too great for Ab treatment (35-37).

One hundred microliters of $10^5$ viable cells/ml 4T1 cell suspension was subcutaneously inoculated in the right abdominal mammary gland of eight-week-old female BALB/c mice, Three days after implanting the 4T1 tumor cells, twenty mice were divided into two groups randomly, and received an intraperitoneal administration of either purified JAA-F11 mAb (120 µg/100 µl/mouse) as treatment or PBS as control twice weekly.

On the fourteenth day after implanting 4T1 tumor, the primary breast tumors were surgically removed. The mouse weights were measured and the weight loss rates were compared between, the treated and control mice. Clinical symptoms, such as lack of grooming, rough coat, rapid and labored breathing, and loss of mobility were monitored, and recorded and used as indicators of morbidity. Mice were sacrificed when weight loss reached 20%, or when significant morbidity occurred. Daily observations were made by both investigators and animal caretakers. The survival time was analyzed using a Kaplan-Meier Survival Curve (MedCalc). The organs of interest (primary tumor, lung, liver, spleen, lymph node, and brain) were collected and immunohistochemical staining was performed. Briefly, the selected tissues were fixed in Z-fixative (Zinc Formalin: Formaldehyde 3.7%, Zinc Sulfate, obtained from Histology Core Lab) with a volume at least 20 times that of the specimen. After 24 hours, fixed tissues were sent to the Histology Service Laboratory to be paraffin-embedded, cut into sections, and placed onto glass slides. A Peroxidase-linked M.O.M. Immunodetection Kit (Vector Labs, Burlingame Calif.) was performed to detect the expression of TF-Ag on the primary tumors and the metastasic lesions from our animal experiments. The tissue sections were deparaffinized and rehydrated using standard protocols. The endogenous peroxidase activity was blocked by incubating the tissue sections with 3% hydrogen peroxide in tap water for 5 min. The sections were washed twice for 2 minutes in PBS. The M.O.M. kit was used as directed with purified JAA-F11 antibody (0.24 mg/ml) in M.O.M. Diluent for 1 hour used in the primary antibody step.

For in vivo immunotherapy after primary tumor removal, forty mice were used, 20 receiving PBS as a control and 20 receiving JAA-F11. On the fourteenth day after implantation the primary breast tumors were surgically removed. The weight changes of mice were measured twice a week and the mice were sacrificed when the weight loss reached 20% or significant morbidity occurred.

Figure 5:
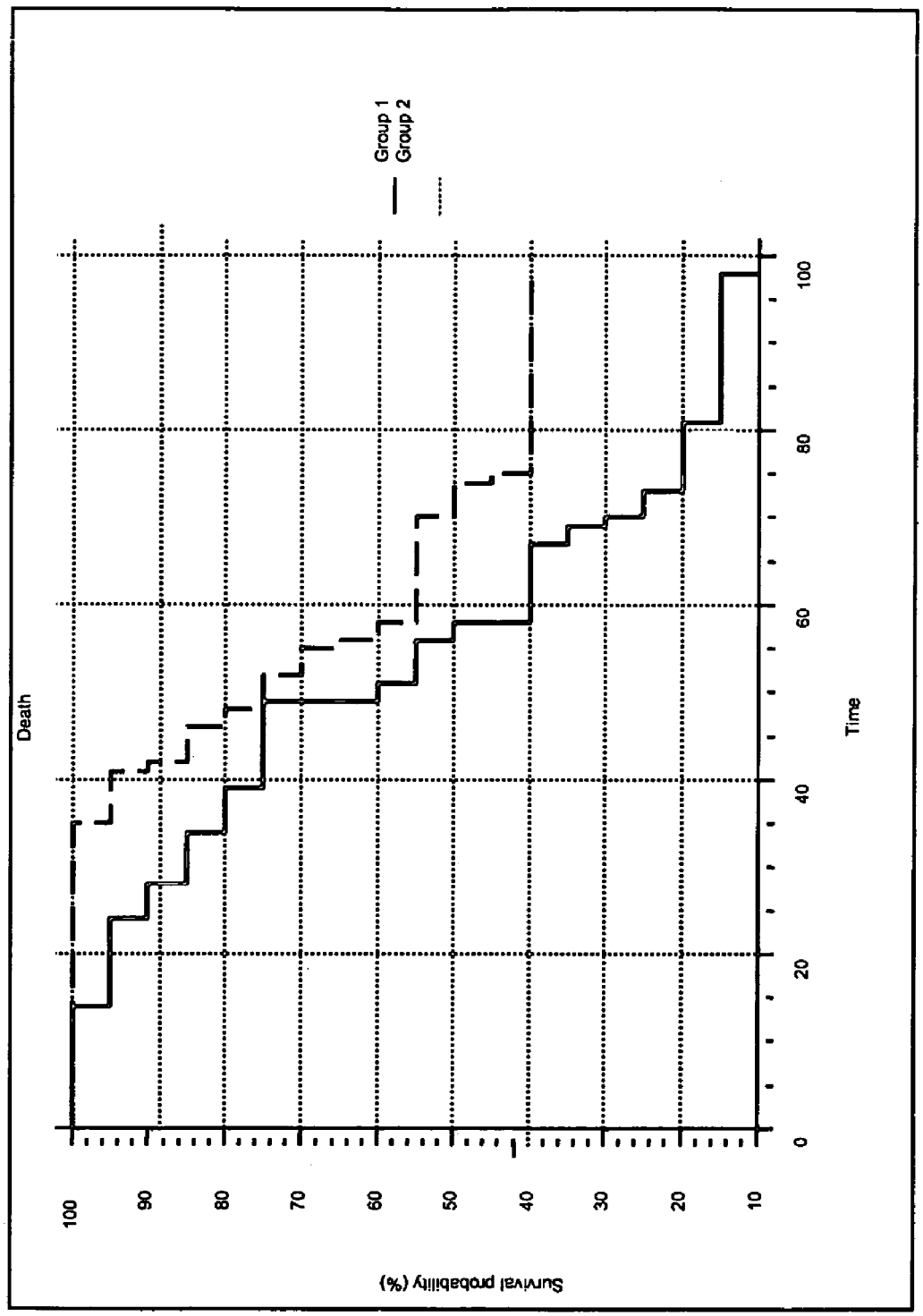
FIG. 5 is a graphical representation of results from a Kaplan-Meier survival curve generated from an in vivo experiment using mice (Group 1: PBS control; Group 0.2: JAA-F11 treatment). The results show that there is a significant (p=0.05) survival advantage to treatment with JAA-F11.

The survival time was recorded and is depicted in FIG. 5. These data were analyzed by the Kaplan-Meier Survival Curve (MedCalc). The median survival time of the PBS and JAA-F11 groups were 57 and 72 days respectively. The difference was significant ($P=0.05$). The animals of JAA-F11 treatment group lived significantly longer than the PBS control group. The organs of interest, such as primary tumor, lung, liver, brain, and spleen were collected. Metastatic lesions were found on lymph nodes, ribs, pericardium, and lungs in mice from both groups.

Figure 6:
FIG. 6A is a photographic representation of lungs from PBS treated and JAA-F11 treated mice.
FIG. 6B shows lung from mice in the JAA-F11 group. Arrows point to the metastatic foci. The photographs demonstrate that there is a significant decrease in the number of visible metastatic foci on the lungs of JAA-F11 treated mice.
Figure 6:
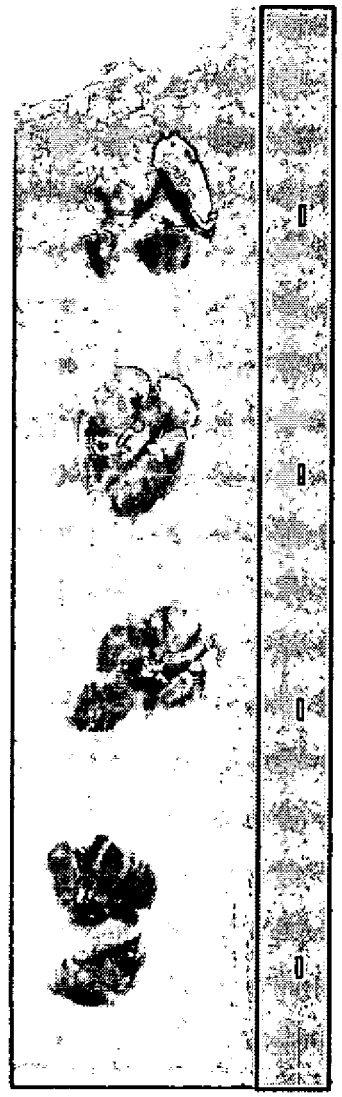

Further, the JAA-F11 treated mice had significantly lower numbers of grossly apparent metastatic lesions in their lungs, with representative lungs shown in FIG. 6. The levels of metastases on lungs were classified into four groups after counting the number of metastatic lesion grossly visible in the lungs (Table 1). The Chi-Square Test (MedCalc) was performed to detect if the frequencies of metastasis levels on lungs from PBS and JAA-F11 group were significantly different. As can be seen in Table 1, the difference between the JAA-F11 group and PBS group is significant ($P=0.0155$). The mice receiving JAA-F11 treatment had less metastasis to the lungs than those receiving PBS control. The lungs that were grossly negative for tumor metastasis were examined for micrometastasis by a pathologist in a blinded study with several lungs with metastatic lesions. Of the two mice in the PBS control group "no metastases observed" group, one had histologically apparent tumor nodules, while the other did not. Of the 10/19 sets of lungs retrieved from the JAA-F11 "no metastases observed" group, 2 were from mice that had died due to tumor load, and these

TABLE 1

Summary of the Levels of Metastases on Lungs

Figure 7:
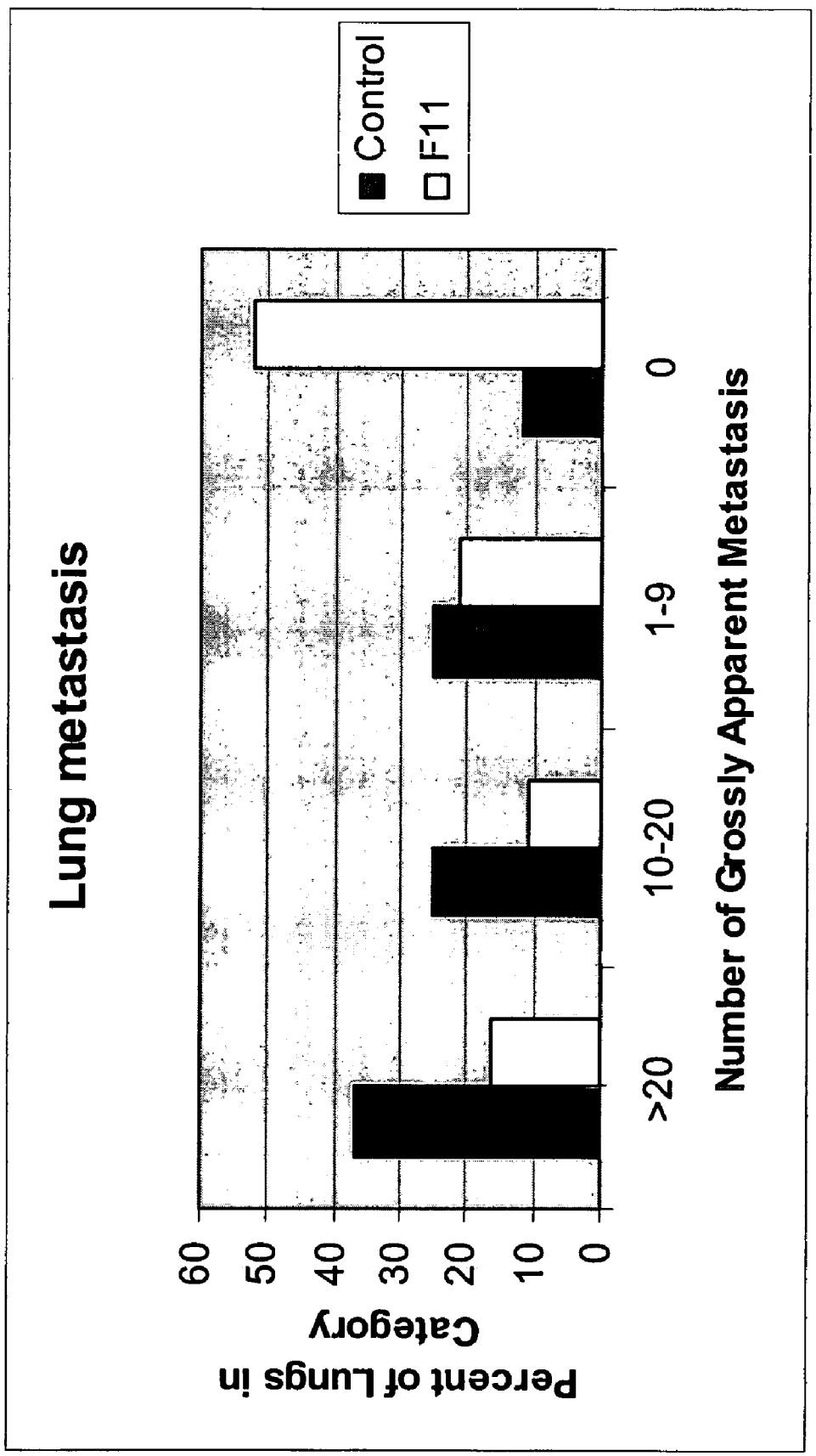
FIG. 7 is a graphical representation of inhibition of metastatsis results from PBS treated and JAA-F11 treated mice.

| # Metastases on lungs | Mice in PBS group | Mice in JAA-F11 group |
|---|---|---|
| +++ (>20) | 6/16 (37.50%) | 3/19 (15.79%) |
| ++ (10-20) | 4/16 (25.00%) | 2/19 (10.53%) |
| + (1-9) | 4/16 (25.00%) | 4/19 (21.05%) |
| − (no metastases observed) | 2/16 (12.50%) | 10/19 (52.63%) | did have microscopic evidence of tumor. The lungs from the 8 mice that had no evidence of disease at the time of the termination of the experiment had no histological evidence of disease in their lungs, thus they were negative for tumor development as analyzed by histological sectioning. Thus, JAA-F11 significantly prolongs survival of mice receiving the treatment (FIG. 5) and inhibits metastasis to lungs ($P=0.016$) (FIGS. 6 and 7, and Table 1).

In summary, the in vitro and in vivo experiments described herein demonstrate that administration of mAb JAA-F11 can inhibit cell adhesion in models of human cancer cell metastasis, mAb JAA-F11 can significantl inhibit metastasis to lungs, and prolong survival of mice after implantation of 4T1 breast cancer cells and resection of the primary tumor. This indicates administration of JAA-F11 mAb is therapeutically useful in two ways: 1) through the traditional antibody mediated selective killing of tumor cells and 2) by decreasing the ability of the tumor cells to metastasize by blocking TF-Ag to lectin adhesion in endothelium and elsewhere.

This invention has been described through examples presented above. Routine modifications to the methods and compositions presented herein will be apparent to those skilled in the art and are intended to be within the scope of the claims appended hereto.

REFERENCES

1. Springer, G F, et al., Journal of the National Cancer Institute 1975; 54(2):335-9.
2. Dippold, W, et al., Environmental Health Perspectives 1990;88:255-7.
3. Maclean, G. D, et al., Seminar in Cancer Biology 1991; 2:433-439.
4. Glinsky, V V, et al., Cancer Research 2001;61: 4851-4857.
5. Glinsky, V V, et al., Cancer Research 2000;60: 2584-2588.
6. Springer, G F, et al., Journal of Biological Chemistry 1983;258:57027-5706.
7. Springer, G F, et al., Journal of Biological Chemistry 1982;257(6):2744-6.
8. Springer, G F. et al., Critical Reviews in Oncogenesis 1995;6:57-85.

9. Takanami, I., Oncology Reports 1999;6:341-4.
10. Schirrmacher, V, et al., Journal of Experimental Medicine 1980;151(4):984-989.
11. Springer, G F., Science 1984;224:1198-1206.
12. Wolf, M F, et al., Tumor Biology 1988;9:190-194.
13. Wolf, M F, et al., Cancer Research 1986;46:1779-1782.
14. Zanetti, M, et al., International Immunology 1993;5:113-119.
15. Springer, G F, et al., Cancer Biotherapy 1994;9:7-15.
16. Avichezer, D, et al., International Journal of Cancer 1997;72(1):119-27.
17. Gabius, H J, et al., Journal of Histochemistry and Cytochemistry 1990;38:1625-1631.
18. Choufani, G, et al., Cancer 1999;86:2353-63.
19. Shigeoka, H, et al., Tumour Biology 1999;20(3):139-46.
20. Kishikawa, T, et al., Japanese Journal of Cancer Research 1999;90:326-32.
21. Rittenhouse-Diakun, K, et al., Hybridoma 1998;17(2):165-173.
22. Dessureault, S, et al., Breast Cancer Research & Treatment 1997;45(1):29-37.
23. Diakun, K R, et al., Immunological Investigations 1987;16:151-163.
24. Franklin, W A. Cancer 1983;51:295-300.
25. Howard, D R, et al., Science 1980;210:201-203.
26. O'Boyle, K P, et al., Cancer Research 1992;52(20):5663-7.
27. O'Boyle, K P, et al., Hybridoma 1996;15(6):401-8.
28. Holmberg, L A, et al., Bone Marrow Transplantation 2000;25(12):1233-41.
29. Holmberg, L A, et al., Expert Opinion on Biological Therapy 2001;1(5):881-91.
30. Longenecker, B, et al., Journal of the National Cancer Institute 1987;78: 489-496.
31. Gilewski, T, et al., Proceedings of the National Academy of Sciences of the United States of America 2001;98(6):3270-5.
32. Rood, P M L, et al., European Journal of Clinical Investigation 2000;30:618-629.
33. Glinskii, O V, et al., Clinical and Experimental Metastasis 2003;20:451-458.
34. Glinskii, O V, et al., Journal of Physiology (London) 2004;554:89-99.
35. Aslakson, C J, et al., Cancer Research 1992;52:1399-1405.
36. Pulaski, B A, et al., Cancer Research 1998;58:1486-1493.
37. Pulaski, B A, et al., Cancer Research 2000;60:2710-2715.
38. Chao, T-Y, et al., In Vitro Cellular and Developmental Biology 1989;25(7):621-626.
39. Bertram, J S, et al., Cancer Letter 1980; 11:63-73.
40. Sharma, S, et al., Journal of Immunology 1999;163: 5020-5028.
41. O'Toole, S A, et al., Cancer Detection & Prevention 2003;27(1):47-54.
42. Johnson, T A, et al., International Journal of Cancer 2000;85(1):104-12.

The invention claimed is:

1. A method for inhibiting in an individual metastasis of metastatic tumor cells, wherein the metastatic tumor cells express TF-Ag molecules, comprising administering to the individual an amount of monoclonal antibody JAA-F11 or an antigen binding fragment thereof sufficient to inhibit the metastasis of the metastatic tumor cells expressing the TF-Ag molecules, such that the metastasis of the cells expressing the TF-Ag molecules is inhibited.

2. The method of claim 1, wherein the antigen binding fragment is selected from the group consisting of Fab, Fab', $F(ab')_2$, and Fv.

3. The method of claim 1, wherein the cells expressing the TF-Ag molecules are selected from the group consisting of breast cancer cells, lung cancer cells, prostate cancer cells and pancreas cancer cells.

4. The method of claim 1, wherein the monoclonal antibody JAA-F11 is humanized.

5. The method of claim 1, wherein the monoclonal antibody JAA-F11 is conjugated to an agent selected from the group consisting of toxins and radioactive isotopes.

6. The method of claim 5, wherein the toxin is selected from the group consisting of diphtheria A chain and ricin A chain.

7. The method of claim 5, wherein the radioactive isotope is selected from the group consisting of, $I^{123}$, $I^{125}$ $I^{124}$ and $I^{131}$.

8. The method of claim 1, wherein the monoclonal antibody JAA-F11 is administered simultaneously or sequentially with a chemotherapeutic agent.

9. The method of claim 1, wherein the monoclonal antibody JAA-F11 is administered by a route selected from the group consisting of parenteral, subcutaneous, intraperitoneal, intravenous, intralymphatic and intrapulmonary administration.

10. The method of claim 1, wherein the metastatic tumor cells are carcinoma cells.

* * * * *